(12) United States Patent
Wang et al.

(10) Patent No.: US 7,247,271 B2
(45) Date of Patent: Jul. 24, 2007

(54) COMPACT CERAMIC SENSOR FOR FUEL VOLATILITY AND OXYGENATE CONCENTRATION

(75) Inventors: Da Yu Wang, Troy, MI (US); David K. Lambert, Sterling Heights, MI (US)

(73) Assignee: Delphi Technologies, Inc., Troy, MI (US)

( * ) Notice: Subject to any disclaimer, the term of this patent is extended or adjusted under 35 U.S.C. 154(b) by 712 days.

(21) Appl. No.: 10/388,777

(22) Filed: Mar. 14, 2003

(65) Prior Publication Data
US 2004/0178069 A1   Sep. 16, 2004

(51) Int. Cl.
  *B32B 5/02* (2006.01)
  *B32B 27/04* (2006.01)
  *B32B 27/12* (2006.01)
  *G01N 27/00* (2006.01)
  *G01N 15/06* (2006.01)

(52) U.S. Cl. .................. 422/82.01; 436/149; 436/150; 436/151; 73/1.01; 73/1.02; 422/50; 422/83; 422/68.1; 422/98

(58) Field of Classification Search .................. 422/50, 422/83, 68.1, 82.01, 98; 73/1.01, 1.02; 436/149, 436/150, 151
See application file for complete search history.

(56) References Cited

U.S. PATENT DOCUMENTS

| | | | |
|---|---|---|---|
| 6,463,789 B2 * | 10/2002 | Moos et al. | 73/31.06 |
| 6,564,624 B2 | 5/2003 | Lin et al. | |
| 6,588,253 B2 | 7/2003 | Lambert et al. | |
| 6,781,388 B2 * | 8/2004 | Wang et al. | 324/690 |
| 6,984,298 B2 * | 1/2006 | Polikarpus et al. | 204/424 |

* cited by examiner

*Primary Examiner*—Brian Sines
(74) *Attorney, Agent, or Firm*—Paul L. Marshall

(57) ABSTRACT

A compact ceramic fuel property sensor comprises a plurality of laminated ceramic layers. The heater, temperature sensor, and capacitance measurement electrodes are embedded between the layers. The capacitance electrodes include interdigitated electrodes and fuel traps for containing a sample of liquid fuel disposed between the interdigitated electrodes. The dimensions of the fuel traps are selected so that the fuel traps remain filled with liquid after said sensor has been bathed in fuel. A method for monolithically preparing the sensors provides a reduced cost method and a sensor that can survive indefinitely in liquid fuel.

4 Claims, 5 Drawing Sheets

COMPACT CERAMIC SENSOR FOR FUEL VOLATILITY AND OXYGENATE CONCENTRATION

TECHNICAL FIELD

The present invention relates to an on-board sensing element for measuring fuel volatility and ethanol concentration. The invention further relates to a method for preparing the on-board sensing element.

BACKGROUND OF THE INVENTION

One way to decrease the quantity of harmful species emitted in engine exhaust, such as hydrocarbons and carbon monoxide, is to better control the engine's air-to-fuel ratio during the cold start period. Such control can be improved if the volatility of the fuel is known. To obtain satisfactory engine performance and low emissions, it is also important to know the concentration of ethanol in the fuel. If the concentration of ethanol and the volatility of the fuel are known, the engine calibration can be optimized to provide satisfactory performance while controlling the hydrocarbons in the exhaust emissions.

The ethanol concentration in gasoline can be determined by measuring the capacitance between electrodes that produce an electric field in a volume that contains a sample of the fuel. The dielectric constant of gasoline fuel that contains ethanol increases with ethanol concentration. The volatility of fuel can also be found by heating a fuel sample and monitoring its evaporation as a function of temperature (or time) by measuring the capacitance between electrodes. As the sample evaporates, liquid fuel with a dielectric constant greater than about 2 is replaced by a mixture of air and fuel vapor that has a dielectric constant of approximately 1.

Sensor structures are known that can be used to measure a fuel's ethanol concentration and volatility. One approach has used closely spaced parallel plates. The gap between the plates is filled with liquid fuel while the structure is at ambient temperature by contacting the structure with liquid fuel and allowing the liquid fuel to be drawn between the plates by the capillary effect. The capacitance measured with the gap filled with liquid fuel determines the concentration of ethanol in the fuel.

To determine fuel volatility with such a structure, electrical current is passed through a heater to raise the temperature of the fuel sample. The temperature is monitored as a temperature dependent resistance. The increase in temperature causes the fuel sample to evaporate. Measured temperature and capacitance as functions of time are used to quantify the evaporation of the fuel sample. Such data are used to determine a measure of the volatility of the fuel. Driveability index (DI) is one such measure of fuel volatility.

However, devices of this type that have been demonstrated are costly to fabricate. One source of difficulty has been the effect of fuels, which are solvents, on the glues or adhesives used to join the heater, which is typically a ceramic, with the other components of the sensor. Another source of difficulty has been the effect of the repeated thermal cycling, required by the measurement, on the adhesives.

SUMMARY OF THE INVENTION

The invention provides a practical means to achieve the above described sensing tasks without the drawbacks of expensive fabrication and short lifetime. A fuel property sensor of the present invention comprises a plurality of laminated dielectric (preferably, ceramic) layers including at least one of each of a heater, a temperature sensor; and a plurality of capacitance measurement electrodes embedded between the layers. The capacitance electrodes include interdigitated electrodes and fuel traps for containing a sample of liquid fuel disposed between the interdigitated electrodes. The dimensions of the fuel trap are selected such that the fuel traps remain filled with liquid after said sensor has been bathed in fuel. In the present application, the fuel traps are discussed as generally rectangular and selected to have a width d and height h selected so that the fuel traps remain filled with liquid after the sensor has been bathed in fuel. The invention is not limited to fuel traps of any particular shape but rather contemplates fuel traps of any desired shape including rectangular, square, round, oval, or other configuration.

A method for preparing a fuel property sensor to be used with liquid fuel comprises preparing green tapes of insulating materials; cutting the green tapes into desired shapes; forming a heater layer, a temperature sensor layer, and a capacitance electrode layer on the shapes or layers; laminating the layers together to form a laminated tape; cutting the laminated tapes into individual sensor units; and firing the individual sensors.

The present sensor structure is constructed monolithically and without the use of adhesives or glues to join the heater with the other components of the sensor. The present sensor achieves the desired sensing tasks and survives intact in solvent-rich fuel tank environments and remains intact and well-functioning in the face of the repeated thermal cycling required during the measurement function.

These and other features and advantages of the invention will be more fully understood from the following description of certain specific embodiments of the invention taken together with the accompanying drawings.

BRIEF DESCRIPTION OF THE DRAWINGS

Referring now to the drawings, which are meant to be exemplary, not limiting, and wherein like elements are numbered alike.

DESCRIPTION OF THE PREFERRED EMBODIMENT

Figure 1:
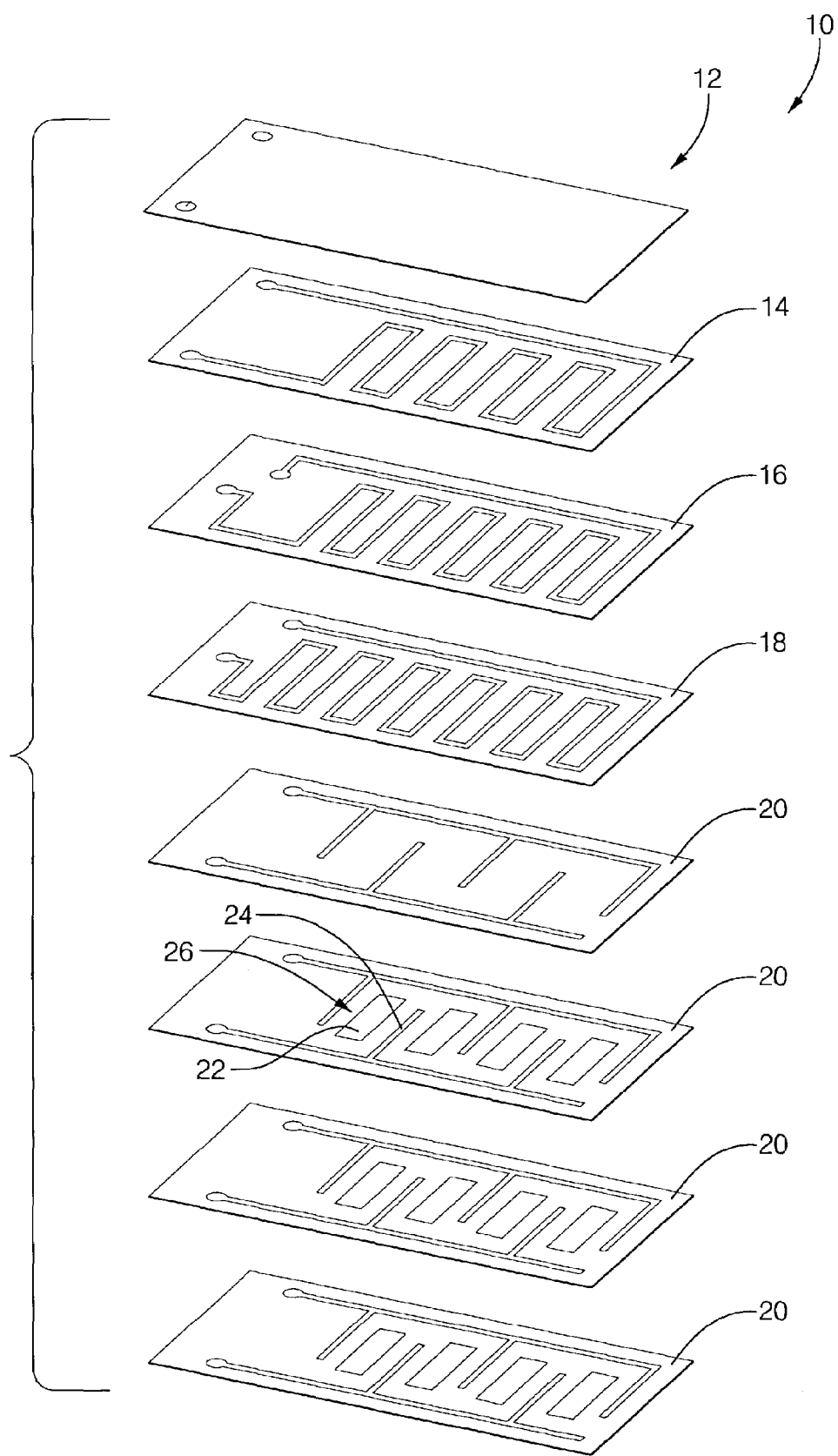
FIG. 1 is an exploded view of a sensor structure layout in accordance with the present invention.

While not limited for use in a vehicle, the present fuel property sensor is particularly suited for use on-board a vehicle and in such application is typically mounted in the fuel tank above the level of the liquid fuel (i.e., in the vapor dome). FIG. 1 illustrates a fuel property sensor 10 according to the present invention comprising a plurality of ceramic layers 12. The heater 14, temperature sensor 16, guard electrode 18, and capacitance measurement electrodes 20 are embedded between the layers 12.

The capacitance measurement electrodes 20 are interdigitated with holes 22 (also referred to herein as "fuel traps" or "slots") between the interdigitated electrode fingers 24 to contain a sample of liquid fuel. The fuel is held within the holes 22 by capillary force.

Figure 2:
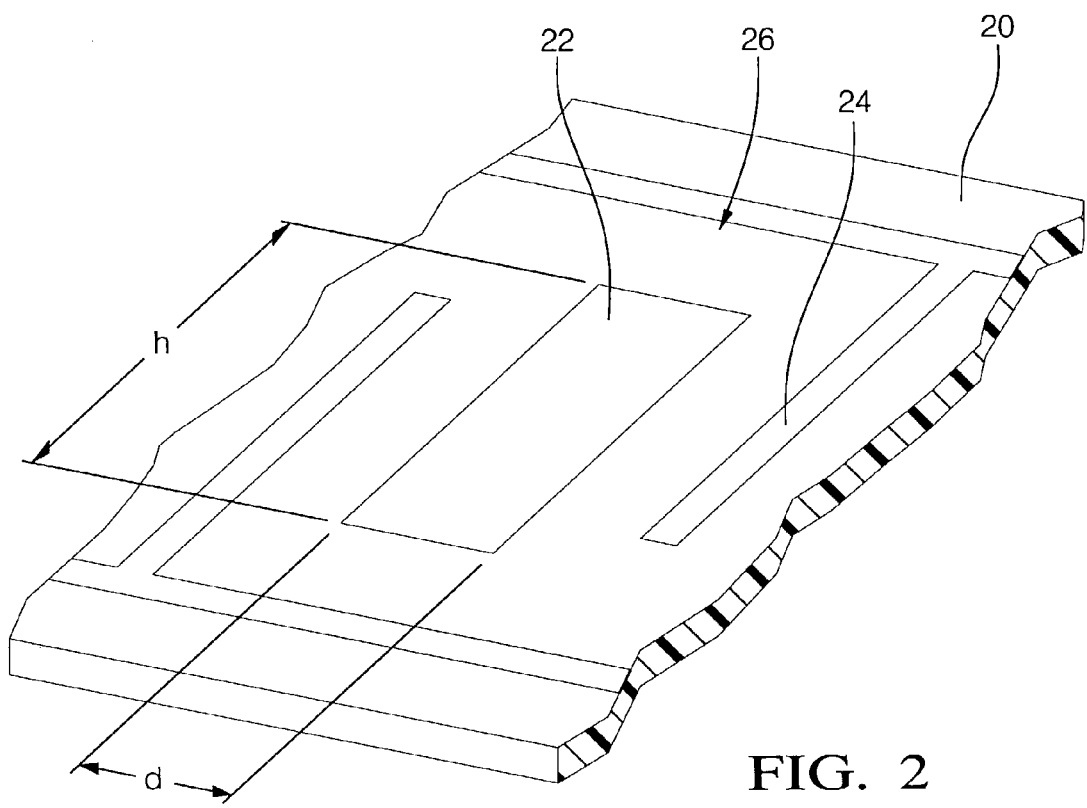
FIG. 2 is an enlarged view of a portion of the sensor structure shown in FIG. 1.

FIG. 2 provides an enlarged view of a portion 26 of a capacitance measurement electrode layer 20 showing an exemplary fuel trap 22. While the fuel traps are discussed with reference to a generally rectangular shaped fuel trap, the invention is not limited to any particular shape and contemplates fuel traps having generally rectangular, square, round, or any other desired shape. Returning to the embodiment shown in FIG. 2, the width d and height h of the fuel traps 22 are chosen so that the fuel traps 22 remain filled with liquid after the sensor element 10 has been bathed in fuel. As an example of a method to estimate the maximum dimensions of the fuel trap, suppose that the ceramic plate 12 is mounted so that its height h extends in the vertical direction. Then h should be less than the distance Q to which the fuel is drawn up into a capillary column between parallel plates, if the distance between the plates is d. The distance Q is a function of the surface tension $\alpha$ of the fuel, the acceleration of gravity g, the density $\rho$ of the fuel, and the contact angle $\theta$ at which the fuel meets the plates. In the approximation that the plates are close together $$Q = \frac{2\alpha}{dg\rho} \cos\theta$$

For gasoline at 20° C., $\alpha=20$ dyne/cm and $\rho=0.75$ g/cm$^3$. The acceleration of gravity is $g=9.8\times10^2$ cm/s$^2$. The contact angle $\theta$ for gasoline in contact with a clean metal surface is approximately 0. We assume that $\theta=0$. Then if $d=200$ μm, $Q=2.7$ cm, so h should be less than 2.7 cm.

Once a prototype device is built, it can be tested to ensure that the fuel trap is filled under all the conditions in which the sensor will be used. If it does not remain filled, then subject to other constraints, either d or h can be decreased until it does remain filled. With gasoline, $d=240$ μm and $h=5$ mm is a suitable combination.

Figure 3:
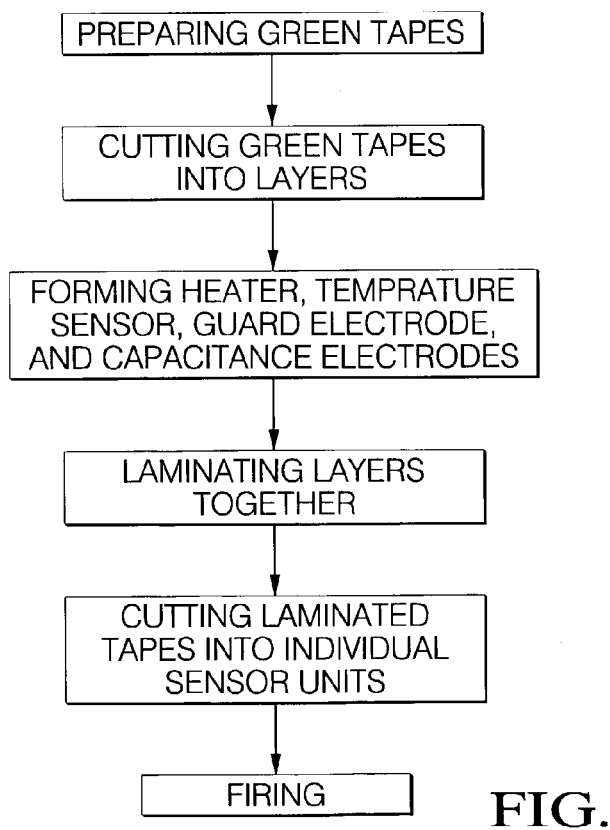
FIG. 3 is a flow chart illustrating the method of the present invention.

In accordance with the method of the present invention, the fuel property sensors 10 are prepared monolithically. FIG. 3 shows generally the steps of the method including preparing green tapes of insulating materials; cutting the green tapes into the desired shapes; screen printing the heater, temperature sensor, guard electrode, and capacitance electrodes; thermally laminating the layers together with a hot press; cutting the laminated tapes into individual sensor units; and firing the sensors. The method saves preparation cost and provides a sensor that can survive indefinitely in liquid fuel.

Figure 4:
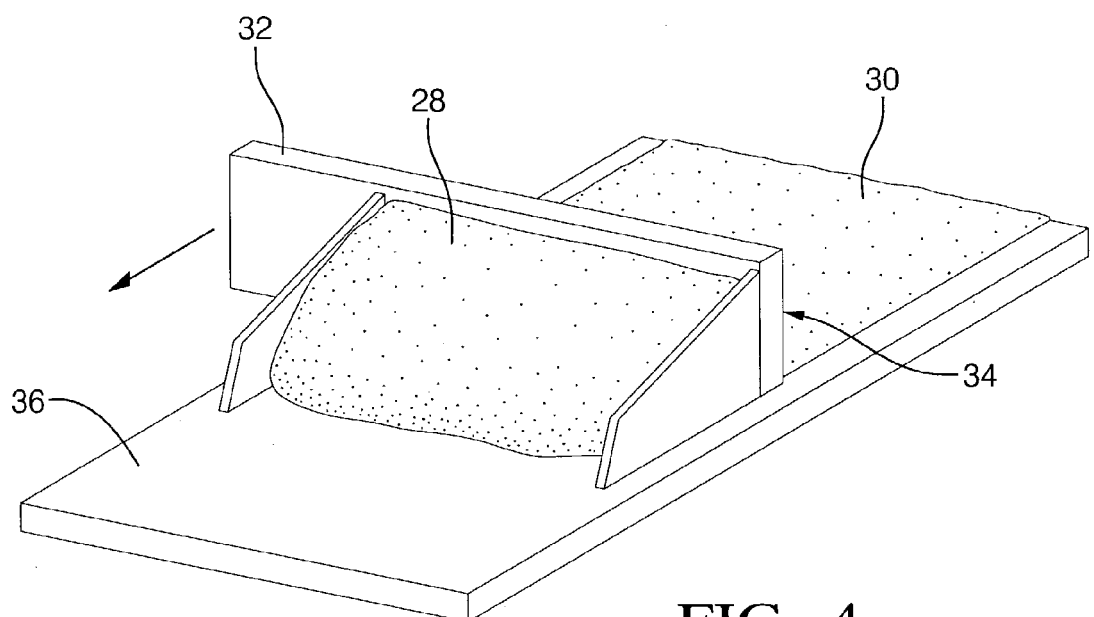
FIG. 4 illustrates a method of making a ceramic tape for the fuel property sensor including depositing a slurry composition on a substrate using a doctor blade according to the present invention.

FIG. 4 illustrates the method for monolithically preparing the fuel property sensor 10 including preparing green tapes of insulating materials. The insulating materials may comprise any suitable insulating material including, but not limited to, alumina, spinet, ceramic oxide, glass, glass-alumina, among others. The insulating material 28 can be mixed with binder, plasticizers, surfactants, foaming agents, other additives, and solvent. The solvent may include deionized water or an organic solvent such as methyl ethyl ketone. The tapes 30 are cast using a doctor blade 32 which may include first and second spaced apart flat legs and an elevated doctor blade knife 34 extending therebetween. The doctor blade 30 can be placed on a substrate 36 such as glass, Mylar®, or other flat surface, from which the cast tape 30 can be easily removed. When the compartment is filled with the insulating material slurry 28, the doctor blade 32 is advanced over the carrier or flat surface to form the cast tape 30.

Figure 5:
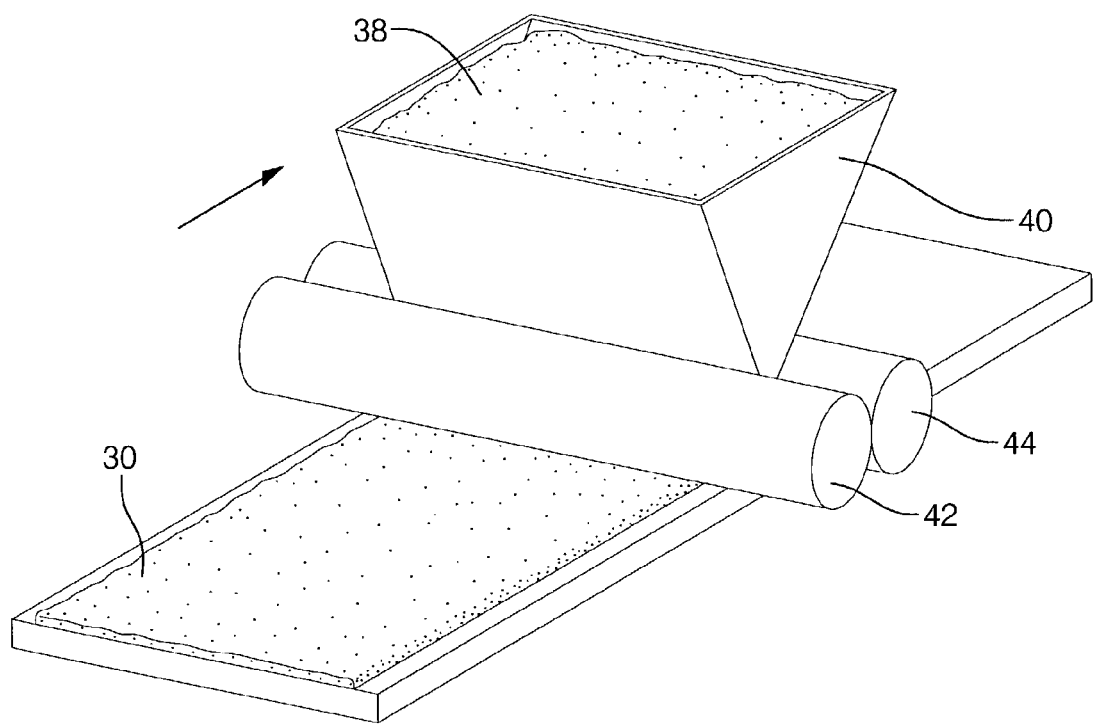
FIG. 5 illustrates a method of making a ceramic tape for the fuel property sensor including delivering a ceramic powder to a roll compaction press according to the present invention.

FIG. 5 illustrates another method for forming the green tapes 30 without solvent by cold pressing the powder. In this method, ceramic powder 38 is placed in a hopper 40 and is continuously fed between two rollers 42, 44 rotating in opposite directions to form a tape 30. After pressing, the tape 30 is cleaned and cut into tiles or tapes 12 of the desired shape.

The heater 14, temperature sensor 16, guard electrode 18, and capacitance electrodes 20 are formed on individual layers by screen printing. The fuel traps 22 are formed using a punch. Unwanted material is punched out of the green ceramic tapes after the interdigitated electrodes have been screen printed.

The layers 12 are laminated together. In a preferred embodiment, the layers 12 are thermally laminated together with a hot press. The laminated tapes are cut into individual sensor units 10. After cutting the laminated tapes into individual sensor units, the sensors 10 are fired in an air furnace or an atmosphere controlled furnace to densify the tapes into their final shape.

The heater materials can be metals, precious metals, or conducting oxides. The same materials can be used for the temperature sensor (the material should have reproducible resistance versus temperature). The same materials can also be used for the guard electrode and the capacitance measurement electrodes.

EXAMPLE

As an example, a sensor element for a fuel property sensor was fabricated using Dupont 951 green tape (commercially available from Dupont) which is alumina based with a glass sintering agent. The electrodes and contacts were prepared by screen printing Dupont 5734 gold ink. For the heater and temperature sensor, a platinum (Pt) ink was used that had been developed by the assignee of the present invention. The Pt ink contains 30% alumina to increase its resistivity after firing. After slots had been cut between the interdigitated electrodes, four such layers were combined with a layer patterned with a guard electrode, a layer patterned with a temperature sensor, a layer patterned with a heater, and a top layer, as shown in FIG. 1, and they were hot pressed together. The sensor element was fired at about 850° C. in air for 15 minutes.

To perform the three-terminal capacitance measurement in the laboratory, a GenRad 1615-A capacitance bridge was used. The bridge was excited by the internal oscillator in a Princeton Applied Research 124A lock-in amplifier at about 10 KHz. The lock-in amplifier was also used to measure the output of the bridge. The capacitance with the sensor element empty or filled with gasoline was determined by manually nulling the bridge. The variation of capacitance as a function of temperature and time as the sensor element was heated was determined from the analog output of the lock-in. An interface circuit for such a sensor that would be suitable for use on a vehicle is described in U.S. Pat. No. 6,469,524 entitled "System and method for interrogating a capacitive sensor" to Larry M. Oberdeir, issued Oct. 22, 2002 to the assignee of the present invention.

The sensor element was 1 centimeter wide, 2 centimeters long and 1.2 millimeters thick. It had 15 fuel traps that were each 5 millimeters long, 0.24 millimeters wide and 0.5 millimeters deep. With the guard electrode grounded, and without any gasoline in the fuel traps, the total three-terminal capacitance between the interdigitated electrodes was measured to be 2.60 pF. With the fuel traps filled with gasoline, the measured capacitance increased to 2.94 pF. Current was passed through the heater to evaporate the gasoline in the fuel traps. After the gasoline had completely evaporated, the measured capacitance returned to 2.60 pF.

As an alternative fabrication technique, the layers are first laminated together, and slots (fuel traps) 22 are then cut through the entire device before it is fired. This requires that the heater, temperature sensor, and guard layers be laid out so that their conducting patterns avoid the slots 22.

Other fabrication techniques are known in the art that can also be used to prepare the device geometry. Fabrication of conducting layers that function as electrodes, heaters, and thermometers is simplified by the planar structure of the device. The conducting layers could, for example, be prepared by evaporation, sputtering, chemical vapor deposition, or stenciling. The conducting layers could be patterned by techniques known in the art such as photolithography, the use of a contact mask during deposition, or by lift-off. Other dielectric materials are also known in the art that could be used for the substrate. These include ceramics, glasses, polymers, semiconductors, and dielectric composites. Methods to prepare slots or holes in an insulating substrate that are known in the art include cutting, punching, machining, etching, ion milling, and sand blasting.

Figure 6:
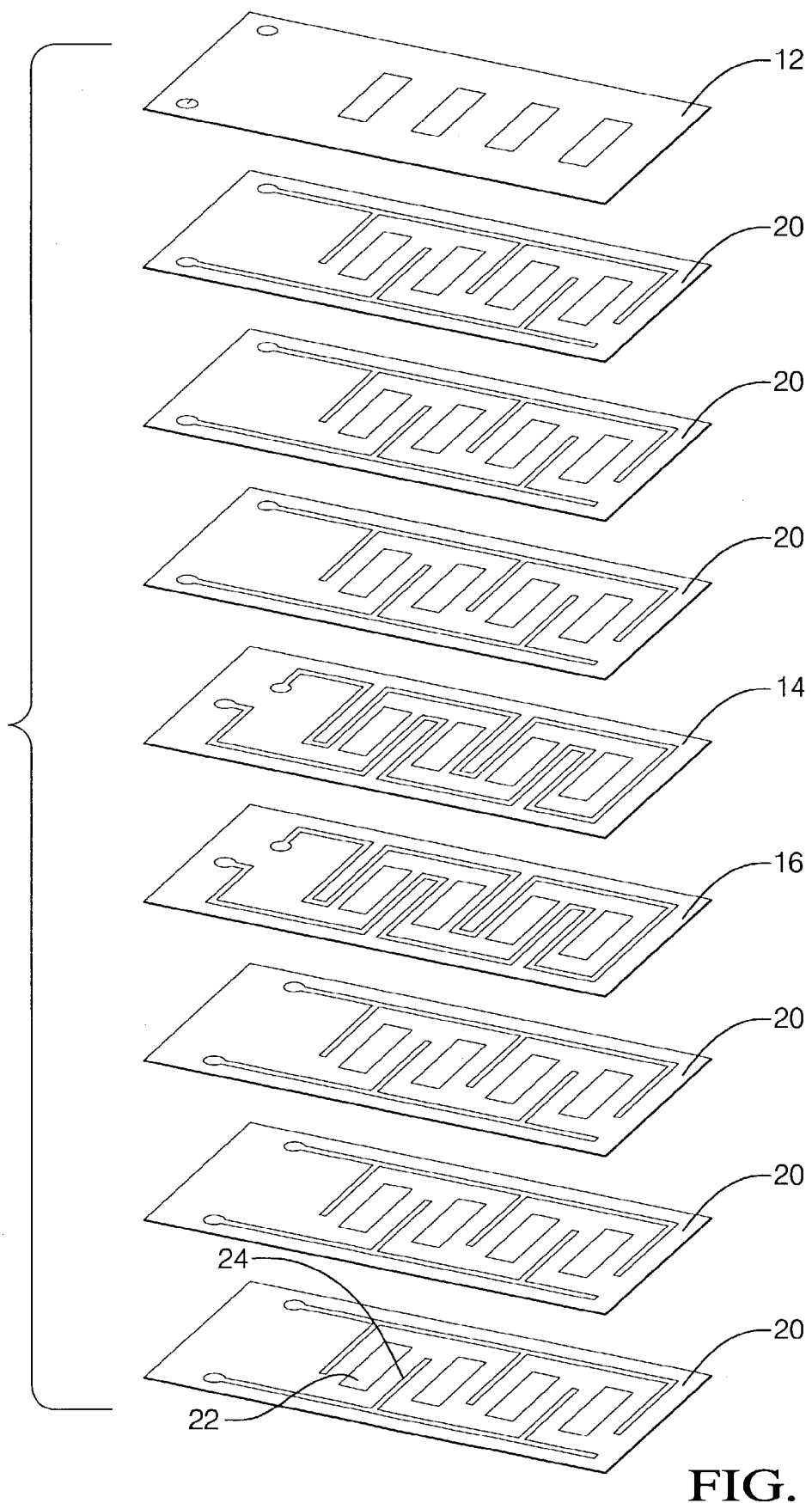
FIG. 6 is an exploded view of another embodiment of the sensor structure layout in accordance with the present invention.

The layers can also be arranged in a different order than shown in FIG. 1. For example, as shown in FIG. 6, the heater layer 14 can be at the center of the structure 10 with the layers that contain interdigitated electrodes 20 symmetrically disposed on the top and bottom of the structure 10. To provide a symmetrical structure, a ceramic layer 12 that has holes 22 but not interdigitated electrodes 24 covers the top layer of interdigitated electrodes.

It is possible to combine the functions of heater and temperature sensor so the heater functions as both heater and temperature sensor. If one lead of the heater is connected to ground, it can also serve as the guard electrode.

Figure 7:
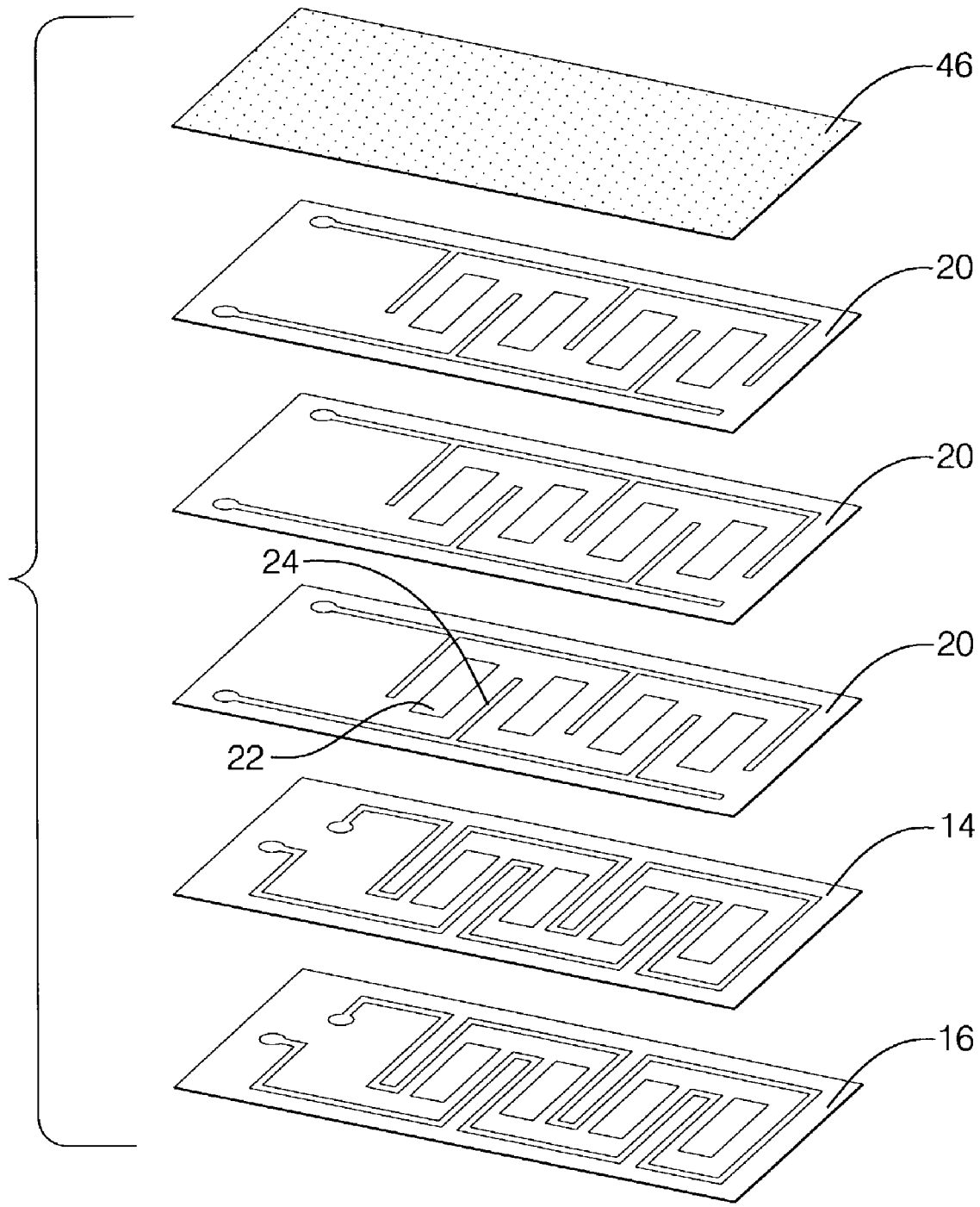
FIG. 7 is an exploded view of yet another embodiment of the sensor structure layout in accordance with the present invention.

As shown in FIG. 7, the outer layer of interdigitated electrodes can be covered by a glazing material 46 to avoid the pick-up of in-phase impedance from the fuel (the capacitance is measured by the out-of-phase impedance). The inks to generate such glazing insulation layer are commercially available, with different compositions for different firing temperatures and firing atmospheres.

While the invention has been described by reference to certain preferred embodiments, it should be understood that numerous changes could be made within the spirit and scope of the inventive concepts described. Accordingly, it is intended that the invention not be limited to the disclosed embodiments, but that it have the full scope permitted by the language of the following claims.

The invention claimed is:

1. A sensor comprising:
   a laminated dielectric structure comprising first and second dielectric layers;
   a first capacitance measurement electrode embedded between said first and second dielectric layers;
   a second capacitance measurement electrode embedded between said first and second dielectric layers and spaced apart from the first capacitance measurement electrode;
   a fuel trap comprising an opening formed in at least one of said first and second dielectric layers and disposed between the first and second capacitance measurement electrodes, said fuel trap being sized and shaped for receiving and containing a sample of liquid fuel.

2. The sensor of claim 1, further comprising a heater layer adapted for heating the sample within the fuel trap.

3. The sensor of claim 1, wherein said first capacitance measurement electrode and said second capacitance measurement electrode are disposed in an interdigitated arrangement.

4. The sensor of claim 1, wherein the dielectric layers are formed of a ceramic material.

* * * * *